United States Patent [19]
Berlin

[11] Patent Number: 5,876,202
[45] Date of Patent: Mar. 2, 1999

[54] STAGGER CUT TEETH

[75] Inventor: Pierre Berlin, La Chaux-de-Fonds, Switzerland

[73] Assignee: Jean-Claude Rouiller, La Chaux-de-Fonds, Switzerland

[21] Appl. No.: 79,128

[22] Filed: May 14, 1998

[30] Foreign Application Priority Data

May 15, 1997 [CH] Switzerland ............... 1137/97

[51] Int. Cl.$^6$ .................................. A61K 5/02
[52] U.S. Cl. ............ 433/102; 433/165; 408/230
[58] Field of Search ............... 433/102, 165; 606/80; 408/210, 230

[56] References Cited

U.S. PATENT DOCUMENTS

| | | | |
|---|---|---|---|
| 1,022,838 | 4/1912 | Funk | 433/102 |
| 4,260,379 | 4/1981 | Groves | 433/102 |
| 5,713,736 | 2/1998 | Heath et al. | 433/102 |

FOREIGN PATENT DOCUMENTS 0 330 107 A1  8/1989  European Pat. Off. .

*Primary Examiner*—Cary E. O'Connor
*Attorney, Agent, or Firm*—McGlew and Tuttle

[57] ABSTRACT

The flutes of a drill bit (1) are constituted by helical portions (4) and rectilinear portions (5).

5 Claims, 2 Drawing Sheets

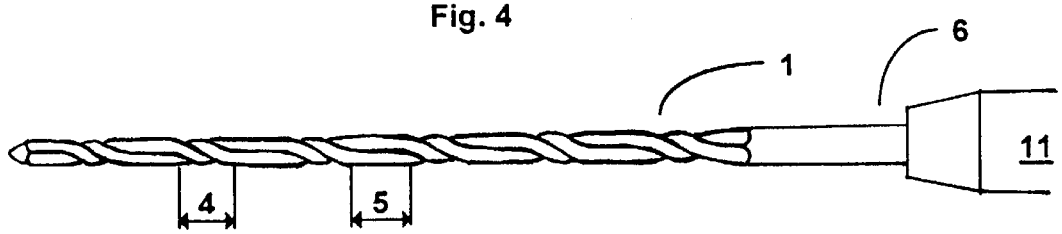
Fig. 4
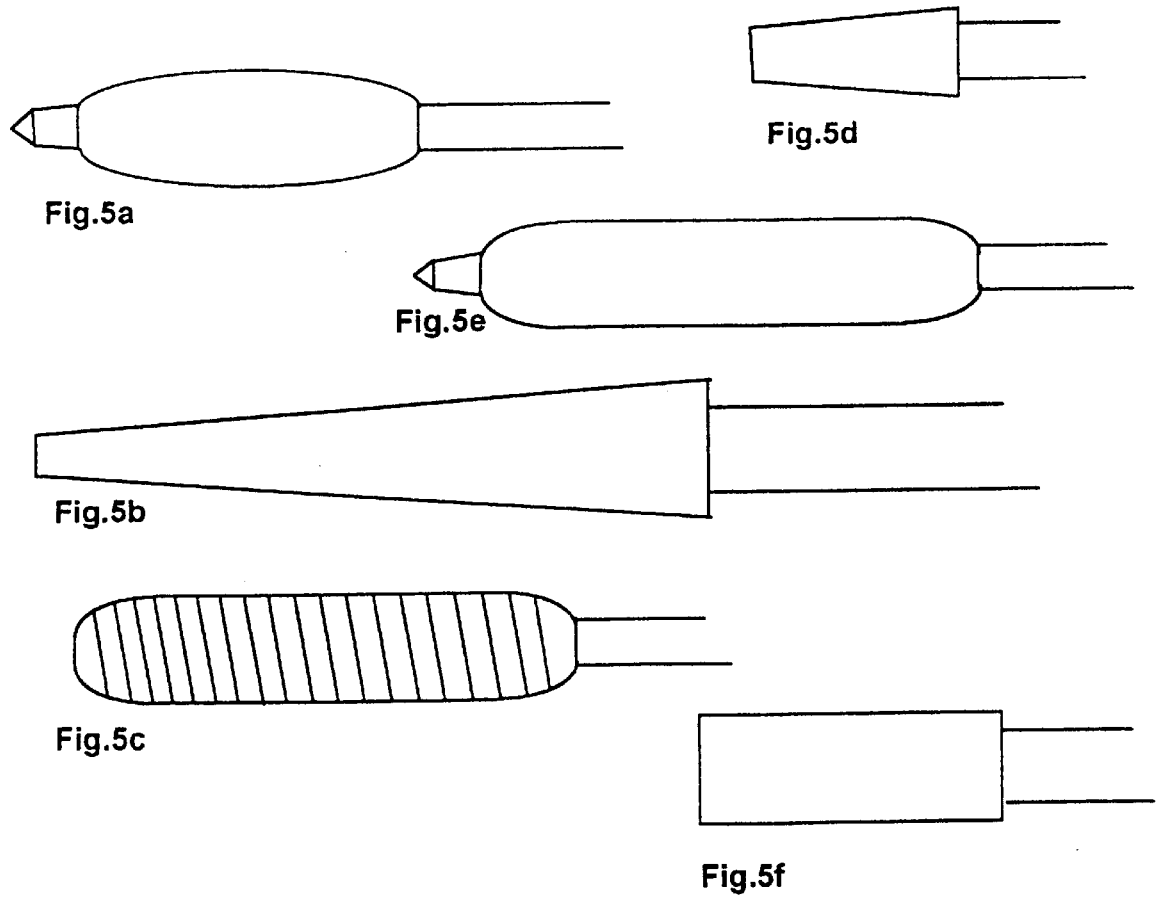
Fig.5a
Fig.5b
Fig.5c
Fig.5d
Fig.5e
Fig.5f

STAGGER CUT TEETH

The present invention concerns a tool having a penetrating end for the removal of material, such tool being mobile around a rotation axis passing through said penetrating end and being further provided with evacuation means comprising at least one peripheral undercut or flute for the material removed.

BACKGROUND OF THE INVENTION

Hand-actuated gimlets are known which enable the providing of lead holes, for example in wood. Likewise known, for piercing the actual hole, are drill bits or twist drills including one or several peripheral undercuts generally in the form of a helix and which begin at the penetrating end of the tool. Such peripheral undercuts, of a generally helical form hereinafter referred to as flutes, serve, on the one hand, to evacuate the chips removed by the cutting portions of the tool. On the other hand when the tool is at least partially conical they serve to enlarge the hole or lead hole by participating in the removal of material by means of their cutting profile. The experienced user of a drill bit takes care to restrain the advance of his tool in order to avoid the undesirable phenomenon of screwing in, by which the advance of the tool is determined simply by the speed of rotation and the pitch of the helix. A perceptible start of screwing in must be corrected by a stopping or reversal of the advance and by slowing, stopping or reversal of the rotation if the tool shows a tendancy to block. Blocking can cause breaking of the tool.

The screwing-in tendency becomes that much stronger to the extent that the tool exhibits a generally conical rather than cylindrical form.

In the special case of dental surgery, the boring of root canals must exhibit a conical profile in view of the filling which will follow. Consequently the tools used have such a strong tendency to screwing in that they are used above all for manually performed axial reaming. Their manipulation is delicate since breaking such a tool can be very detrimental.

Canal boring with continuous driving of the instruments in rotation at low speed is only recently recommended. Such procdure has as principal advantage that of not deforming the natural path of a tooth canal whilst enlarging it.

In such technique it has been attempted to eliminate the screwing-in tendency by blunting the cutting angles of the flutes. But not only is the efficiency of material removal diminished along with undesirable heating but there subsists a certain screwing-in tendency.

DISCUSSION OF THE PRIOR ART

For the difficulties hereinbefore described remedies have been proposed consisting in carrying out the boring in several stages, each by means of a different tool. This has the drawback of multiplying the number of tools and cancelling the time saved relative to the axial reaming method.

The patent document EP 0 330 107 teaches the varying of certain geometric parameters of a conical tool provided with flutes with the objective of avoiding torsional shocks when the tool is engaged. Apart from the fact that the problem to be resolved is different, the low values envisaged cannot overcome the screwing-in tendency.

There thus remains to be found a material-removing tool which, in addition to a zero screwing-in possibility exhibits a steady lateral cutting power capable of effecting a bore in a single pass, and this for all manners of industrial applications.

SUMMARY OF THE INVENTION

The invention proposes to arrive at this result by having the profile of the undercut depend from the distance z to the penetrating end of the tool and being determined by coordinates x, y such that: $x = R \cos a$, $y = \sin a$, $a = f(z)$ and $R = g(z)$ where g is a positive function of z between the values $z > 0$ and $z = z\,max$, and f is a function such that $f(z\,max)$ is greater than $f(0)$.

More specifically, it is proposed for the different peripheral undercut or undercuts, hereinafter called flutes, to adopt a profile which, while permitting evacuation of the material removed by the penetrating end and the profile of such flutes, is not translated by an advancing effect under the rotational action of the tool.

Certain portions of the tool profile exhibit a helix angle to the right as in a standard drill bit. Others to the contrary exhibit a zero helix angle, the flute being rectilinear and parallel to the tool axis, or a helix angle to the left which compensates for the-screwing-in tendency of the portions with the helix angle to the right.

For this reason the form of the profile cannot be described as a function of the helix angle, as in the case of the standard mathematical definition of a helix. To the contrary it is the helix angle a which must be expressed as a function f of the distance z. Such function f will exhibit, in accordance with the results sought, a series of increasing portions separated by constant or decreasing portions. It is however necessary that at the tool end opposite the penetrating end, referenced on the axis by $z = z\,max$, the total helix angle be positive, otherwise the removed material will not be evacuated by the rotational movement of the tool.

R is the radius of the original cross-section of the tool prior to cutting the flute or flutes. It is also a function of z and generally zero for the penetrating end of the tool where $z = 0$.

In the portions in which R is growing as a function of z the tool has the general form of a truncated cone. Such portions exhibit an increased screwing-in tendency.

The invention applies to any values of whatsoever (but. never zero) between $z > 0$ and $z = z\,max$.

Experience shows that a regular alternation of the portions where f is linearly increasing as a function of z and of portions where f is constant as a function of z procure a good resistance against screwing in, whilst maintaining good cutting power and evacuation of removed material.

Such a flute is thus composed of an alternating succession of helical and rectilineal segments.

In a specific embodiment of the invention, the staggered cutting of the flutes previously described is applied to root canal boring instruments for dental surgery.

Such instruments are intended for enlarging root canals. They exhibit a great number of forms, cylindrical or conical, with one, two, three or four flutes having sharp edges for cutting or contrariwise non-cutting edges. In the latter case tools are encountered with concentric margins or with blunted edges. The invention is successfully applicable to all of these embodiments.

In a specific embodiment of the invention, the staggered cutting of the flutes previously described is applied to drills and burrs of all types used in dentistry and bone surgery.

Such types of drills especially comprise:

drills of the so-called gates type;

drills of the so-called Peeso type;

cylindrical drills.

Such types of burrs in particular comprise:

so-called pivot burrs;

so-called overcut burrs for bone;

so-called fissure burrs.

The invention will be better understood in the light of the detailed description to follows having reference to the attached drawings

BRIEF DESCRIPTION OF DRAWINGS

FIG. 4 shows a conical embodiment;

FIG. 5a to 5f show embodiments applied to various forms of burrs.

DESCRIPTION OF THE PREFERRED EMBODIMENTS

Figure 1:
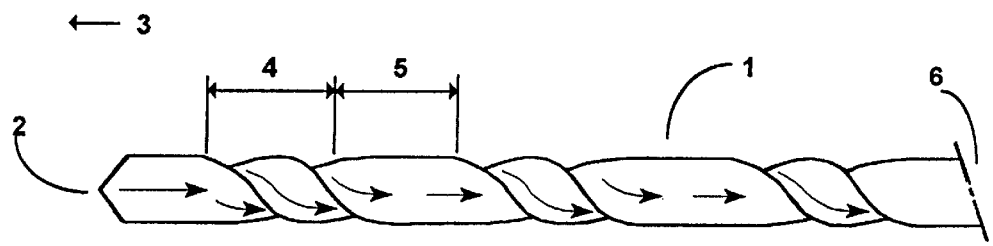
FIG. 1 shows an example of a staggered cut on a cylindrical drill.

On FIG. 1 the tool 1 is provided with a penetrating end 2 and turns on an axis of rotation. Arrow 3 shows the sense of the advance. The profile of the flutes of tool 1 is made up by helical portions 4 and rectilinear portions 5, that is to say, where the helix angle does not vary. In this example the function f increases linearly in the portion 4 and is constant in the portion 5.

The helical portions 4 in a known manner enable the removed material to be caused to advance toward the end 6 opposite the penetrating end 2.

The rectilinear portions 5 have as function the reduction of the screwing-in tendency of tool 1. Such tendency is thus rendered sufficiently slight as to permit the continuous driving in rotation of tool 1.

In cases where required by the conditions of boring, it is possible to replace the rectilinear portions 5 by helical portions in which the value of the helix is reversed relative to portions 4. The function f is then decreasing. It is however advantageous not to have it strongly decreasing since difficulties in evacuation of the removed material will result therefrom.

Portions 5 may also exhibit a smaller value of helix but of the same sense as portions 4. In this manner the removed material is transported in a more regular manner toward the end 6.

Figures 2A, 2B:
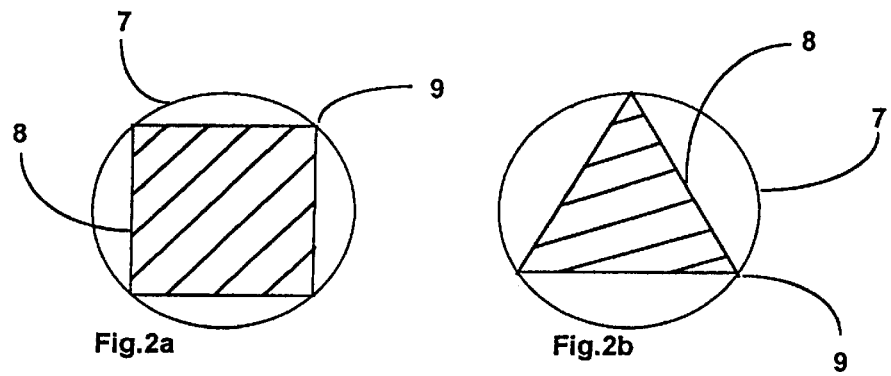
FIG. 2a and 2b show in cross section embodiments with sharp cutting edges.

FIG. 2a shows an embodiment of tool 1 in cross-section perpendicular to the axis joining ends 2 and 6, such embodiment showing four sharp cutting edges 9 defined by four flutes 8 obtained in accordance with the invention. Such four flutes 8 are arranged in the tool in its original form, shown by a circle 7 the radius of which, previously, called R, is a function g of the distance z from the plane of the cross-Section of FIG. 2a to the penetrating end 2.

In a coordinate reference tied to the tool, the running point 9 of the cutting edge has as abscissa, cos a, as ordinate R sin a; the angle a is itself a function designated by f of the distance z from the plane of the cross-section of FIG. 2a to the penetrating end 2. The trace of the penetrating end 2 on FIG. 2a is none other than the center of the circle 7.

The angle a is the helix angle of any one of the flutes 8. In the prior art it increases linearly as a function of z. According to the invention it is a non-linear function f of z, the sole constraint being that f(z max) at the end 6 of tool 1 be greater than f(0) at the penetrating end 2. This is favourable for evacuation of the removed material.

Flute 8 is obtained in a known manner, for example by grinding. In the example shown the grinder will have a diameter much greater than R which gives a rectilinear aspect to flute 8 in the cross-sectional plane of FIG. 2a.

FIG. 2b shows an example similar to that of FIG. 2a but with three flutes rather than four. Except for the different number of flutes, all the explanations remain valid.

The cutting edges 9 of FIGS. 2a and 2b are sharp. This enables allocation of a material removing function to such edges 9, especially for the case in which the original form of the tool is conical.

Figures 3A, 3B, 3C:
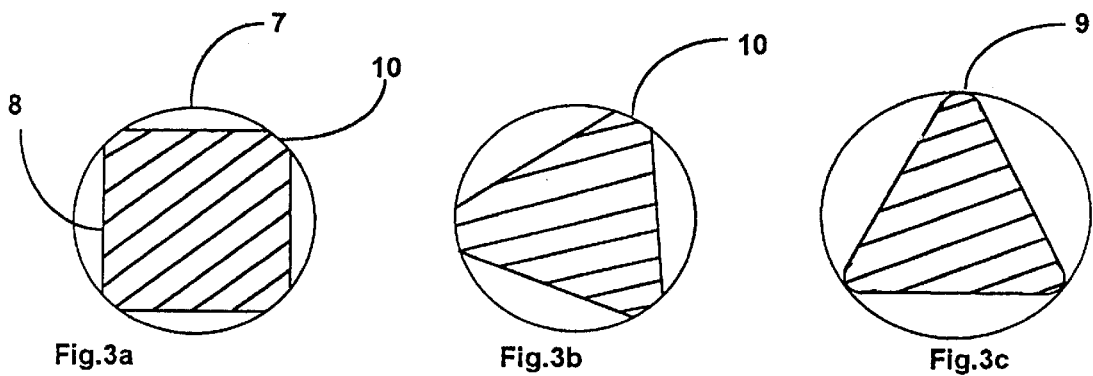
FIG. 3a and 3b show other embodiments with non-cutting edges and concentric margins.
FIG. 3c shows an embodiment with a blunted edge.

FIGS. 3a and 3b illustrate the possibility of forming non-cutting edges 10, said to be with concentric margin. In such embodiment the flutes 8 are less deeply formed in the original circle in a manner known per se, which renders them less cutting.

FIG. 3c shows another manner, known per se, of rendering flutes 9 less cutting by blunting them. Only a single example with three flutes has been shown by the figure.

FIG. 4 shows an embodiment of conical execution in a dental instrument intended for boring root canals. The tool 1 is gripped in a chuck 11, itself driven in rotation by known means.

Tool 1 is supple, this permitting it to follow root canals. The helical portions 4 alternate with the rectilinear portions 5, the original form of the tool being slightly conical. The rounded-off point, referred to as a blunt points enables an improvement in guiding the tool in the root canal.

Alternating the portions 4 and, 5 enables reducing the screwing-in tendency of tool land thus avoids blockages, sources of tool breakage.

FIG. 5 shows the original form of a burr of the "Gates" type. The radius of such a form, measured in the plane of the cross-section perpendicular to the axis of symmetry, is a relatively complex function g of the distance z from such cross-sectional plane to the penetrating end 2. The tendency to screwing in comes from all the portions in which said function g is increasing.

In FIG. 5b, showing a conical burr for a dental pivot, the radius R increases linearly as a function of z. There also it will be useful to choose the function f, determining the helix angle a, as a function of z, as a series of helical portions 4 and rectilinear or quasi-rectilinear portions 5.

FIG. 5c shows a surgical burr intended for bone. The hatching. recalls that such a burr is commonly overcut, that is to say, exhibits one or several first flutes of constant helical angle arranged on the active portion, of generally cylindrical form. The alternative cut, according to the invention consisting in one or several flutes of variable helix angle, is in superposition from such first flutes.

FIG. 5d shows a conical dental burr. The same comments as in the case of FIG. 5b apply to this embodiment which is distinguished by its reduced dimensions.

FIG. 5e illustrates a dental burr of the Peeso type by way of exale of variation of the tool profile to which the invention can apply.

FIG. 5f, showing a cylindrical dental burr, is an embodiment in which not only the penetrating end 2 of the tool exhibits a non-zero radius for z=0, but where such radius R remains constant over a substantial range of values of z.

The examples of FIGS. 5a to 5f constitute merely a sampling of the possibilities of applying the invention to all cases where the screwing-in tendency must be eliminated.

What I claim is:

1. A tool for the removal of material, including a penetrating end, such tool being mobile around a rotation axis passing through such penetrating end, such tool being further provided with evacuation means for the material removed comprising at least one peripheral undercut or flute, the profile of such undercut depending from the distance z to the penetrating end and being determined by coordinates x, y such that: $x=R \cos a$, $y=R \sin a$, $a=f(z)$ and $R=g(z)$ where g is a positive function of z between the values $z>0$ and $z=z$ max, and f is a function such that $f(z$ max$)$ is greater than $f(0)$.

2. A tool as set forth in claim 1, employed as a dental boring instrument for the enlarging of root canals.

3. A tool as set forth in claim 1, such tool being a burr or drill bit employed in dentistry or in bone surgery.

4. A tool as set forth in claim 3, such tool being a burr or drill bit of the Gates or Peeso type, or a dental pivot burr, or an overcut burr for bone, or a conical or cylindrical dental burr.

5. A tool as set forth in claim 1, in which the profile of the undercut or flute is constituted by a succession of helical portions and rectilinear portions.

* * * * *